United States Patent [19]

Enomoto et al.

[11] Patent Number: 5,281,574

[45] Date of Patent: Jan. 25, 1994

[54] URACIL DERIVATIVES AND THEIR USE

[75] Inventors: Masayuki Enomoto; Susumu Takemura, both of Hyogo; Masaharu Sakaki, Osaka; Shinsuke Shojima, Hyogo, all of Japan; Eiki Nagano, Raleigh, N.C.

[73] Assignee: Sumitomo Chemical Company, Limited, Osaka, Japan

[21] Appl. No.: 968,498

[22] Filed: Oct. 29, 1992

[30] Foreign Application Priority Data

Nov. 1, 1991 [JP] Japan .................................. 3-287649

[51] Int. Cl.$^5$ ..................... A01N 43/48; C07D 239/02
[52] U.S. Cl. ..................................... 504/243; 544/309; 544/311; 544/312
[58] Field of Search ................. 504/243; 544/312, 309, 544/311; A01N 43/48

[56] References Cited

U.S. PATENT DOCUMENTS

| | | | |
|---|---|---|---|
| 4,746,352 | 5/1988 | Wenger et al. | 544/311 |
| 4,760,163 | 7/1988 | Wenger et al. | 71/90 |
| 4,812,164 | 3/1989 | Wenger et al. | 71/92 |
| 4,859,229 | 8/1989 | Wenger et al. | 71/93 |
| 4,927,451 | 5/1990 | Brouwer et al. | 71/92 |
| 5,041,156 | 8/1991 | Suchy et al. | 71/92 |
| 5,084,084 | 1/1992 | Satow et al. | 71/93 |
| 5,116,404 | 5/1992 | Ishii et al. | 71/92 |
| 5,127,935 | 7/1992 | Satow et al. | 71/92 |
| 5,134,145 | 7/1992 | Brouwer et al. | 544/313 |

FOREIGN PATENT DOCUMENTS

| | | |
|---|---|---|
| 0408382 | 7/1990 | European Pat. Off. . |
| 420194 | 4/1991 | European Pat. Off. . |
| 9211244 | 7/1982 | Japan . |
| 4193876 | 7/1992 | Japan . |

Primary Examiner—Cecilia Tsang
Attorney, Agent, or Firm—Birch, Stewart, & Birch

[57] ABSTRACT

There is disclosed a 1-phenyl-4 trifluoromethyl-uracil derivative of the general formula:

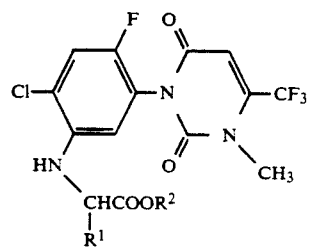

wherein $R^1$ is hydrogen or methyl, and $R^2$ is $C_1$-$C_7$ alkyl or $C_3$-$C_7$ cycloalkyl optionally substituted with $C_1$-$C_3$ alkyl. Also disclosed are a herbicidal composition containing this derivative as an active ingredient and a method for exterminating undesired weeds by application of this herbicidal composition.

13 Claims, No Drawings

URACIL DERIVATIVES AND THEIR USE

FIELD OF THE INVENTION

The present invention relates to novel uracil derivatives and their use, and more particularly, to novel 1-phenyl-4-trifluoromethyluracil derivatives and herbicidal compositions containing these uracil derivatives as an active ingredient.

BACKGROUND OF THE INVENTION

It has hitherto been known that certain kinds of uracil derivatives have herbicidal effects on weeds. For example, it is described in the U.S. Pat. Nos. 4,859,229 and 5,084,084 that some of the particular uracil derivatives exhibit a herbicidal activity.

However, these compounds can hardly be said to be satisfactory herbicides because of their still insufficient herbicidal activity and large application amounts to be required.

SUMMARY OF THE INVENTION

Under these circumstances, the present inventors have intensively studied various compounds and found that particular 1-phenyl-4 trifluoromethyluracil derivatives each containing an amino acid ester group at the 5th position on the phenyl ring have an excellent herbicidal activity, thereby completing the present invention.

According to the present invention, there is provided a 1-phenyl-4-trifluoromethyluracil derivative of the general formula:

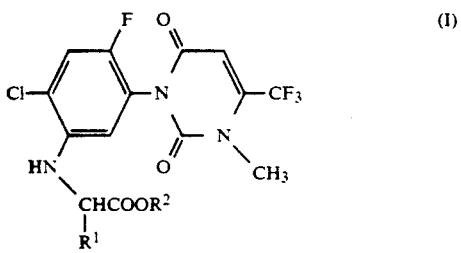
(I)

wherein $R^1$ is hydrogen or methyl, and $R^2$ is $C_1$-$C_7$ alkyl or $C_3$-$C_7$ cycloalkyl optionally substituted with $C_1$-$C_3$ alkyl.

The present invention also provides a herbicidal composition comprising the above uracil derivative (I) as an active ingredient and a method for exterminating undesired weeds, which comprises applying a herbicidally effective amount of the herbicidal composition to the area where undesired weeds grow or will grow.

DETAILED DESCRIPTION OF THE INVENTION

The 1-phenyl-4-trifluoromethyluracil derivative (hereinafter referred to as compound (I)) of the present invention is characterized in that the substituent at the 5th position on the phenyl ring is a group of the formula: $-NHCH(R^1)COOR^2$ wherein $R^1$ is hydrogen or methyl, and $R^2$ is $C_1$-$C_7$ alkyl or $C_3$-$C_7$ cycloalkyl optionally substituted with $C_1$-$C_3$ alkyl. Preferred examples of the compound (I) are those wherein $R^1$ is methyl, and more preferably, those wherein $R^1$ is methyl and $R^2$ is $C_1$-$C_5$ alkyl.

The compound (I) can be produced by reacting a compound of the formula:

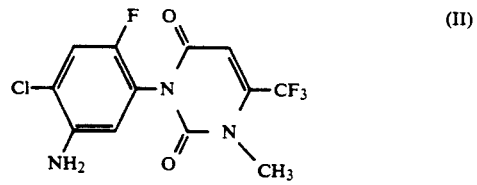
(II)

with a compound of the general formula:

(III)

wherein X is chlorine, bromine or iodine, and $R^1$ and $R^2$ are the same as described above.

This reaction is usually carried out without any solvent or in a solvent at a temperature of $-20°$ C. to 200° C. for a period of 0.1 to 10 hours. The compound (III) is usually used at a proportion of 1 to 5 equivalents to one equivalent of the compound (II).

As the solvent to be used in this reaction, there can be exemplified aromatic hydrocarbons such as toluene; halogenated hydrocarbons such as chloroform and dichloromethane; amides such as N,N-dimethylformamide and N,N-dimethylacetamide; sulfur compounds such as dimethylsulfoxide; and ethers such as 1,4-dioxane and tetrahydrofuran.

After the completion of the reaction, water is added to the reaction mixture, which is then subjected to an ordinary post-treatment such as extraction with an organic solvent and concentration. If necessary, any purification such as chromatography or recrystallization may be further utilized to give the objective compound (I).

The compound (II) as the starting material is described in the U.S. Pat. No. 4,859,229.

In cases where the compound (I) contains an asymmetric carbon, it exhibits optical isomerism, and the corresponding optical isomers should be also included in the scope of the present invention.

The compound (I) of the present invention has an excellent herbicidal activity and also exhibits noticeable selectivity between crop plants and weeds. The compound (I) of the present invention has a herbicidal activity to harmful weeds under the soil or foliar treatment of upland fields, examples of which are broad-leaf weeds such as wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursapastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), sun spurge (*Euphorbia helioscopia*) and spotted spurge (*Euphorbia maculata*); gramineous weeds such as Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), wild oats (*Avena fatua*), Johnsongrass (*Sorghum halepense*), quackgrass (*Agropyron repens*), downy brome (*Bromus tectorum*) and giant foxtail (*Setaria faberi*); commelinaceous weeds such as Asiatic dayflower (*Commelina communis*); and cyperaceous weeds such as rice flatsedge (*Cyperus iria*) and purple nutsedge (*Cyperus rotundus*), whereas it shows no material phytotoxicity to main crops such as corn (*Zea mays*), wheat (*Triticum aestivum*), rice (*Oryza sativa*), soybean (*Glycine max*) and cotton (*Gossypium hirsutum*).

The compound (I) of the present invention also has a herbicidal activity to harmful weeds under the flooding treatment of paddy fields, examples of which are gramineous weeds such as barnyardgrass (*Echinochloa oryzicola*); broadleaf weeds such as common falsepimpernel (*Lindernia procumbens*), Indian toothcup (*Rotala indica*) and waterwort (*Elatine triandra*); cyperaceous weeds such as water nutgrass (*Cyperus serotinus*) and needle spikerush (*Eleocharis acicularis*); and arrowhead (*Sagittaria pygmaea*), whereas it shows no material phytotoxicity to rice (*Oryza sativa*).

Further, the compound (I) of the present invention can be used as an active ingredient of non-selective herbicides to be employed in the controlling weeds of places such as orchards and non-agricultural fields, or in the controlling weeds of upland fields or paddy fields before plowing or crop seeding. because it has particularly excellent herbicidal activity to a wide variety of harmful weeds under the foliar treatment.

When the compound (I) of the present invention is used as an active ingredient of herbicides, it is usually formulated with solid or liquid carriers or diluents as well as surfactants and other auxiliary agents into conventional formulations such as emulsifiable concentrates, wettable powders, flowables, granules and water-dispersible granules.

These formulations contain the compound (I) as an active ingredient at a content within the range of 0.002% to 80% by weight, preferably of 0.01% to 70% by weight.

Examples of the solid carrier or diluent are fine powders or granules of kaolin clay, attapulgite clay, bentonite, terra alba, pyrophyllite, talc, diatomaceous earth, calcite, walnut shell powders, urea, ammonium sulfate and synthetic hydrated silica. As the liquid carrier or diluent, there can be exemplified aromatic hydrocarbons such as xylene and methylnaphthalene; alcohols such as isopropanol, ethylene glycol and cellosolve; ketones such as acetone, cyclohexanone and isophorone; vegetable oils such as soybean oil and cotton seed oil; and dimethylsulfoxide, N,N-dimethylformamide, acetonitrile, water and the like.

Examples of the surfactant used for emulsification, dispersing or spreading are those of anionic type, such as alkylsulfates, alkylsulfonates, alkylarylsulfonates, dialkylsulfosuccinates and phosphates of polyoxyethylene alkylaryl ethers; and those of nonionic type, such as polyoxyethylene alkyl ethers, polyoxyethylene alkylaryl ethers, polyoxyethylene polyoxypropylene block copolymers, sorbitan fatty acid esters and polyoxyethylene sorbitan fatty acid esters.

Examples of the auxiliary agent are ligninsulfonates, alginates, polyvinyl alcohol, gum arabic, carboxymethyl cellulose (CMC) and isopropyl acid phosphate (PAP).

The compound (I) of the present invention is usually formulated in any suitable formulation and used for pre-emergence or post-emergence control of undesired weeds by the soil or foliar treatment for upland fields and by the flooding treatment for paddy fields. The soil treatment includes soil surface treatment and soil incorporation. The foliar treatment is effected by application over the plants or by directed application to the weeds to keep any chemical off the crop foliage.

Further, the compound (I) of the present invention may be used together with any other herbicide to enhance its herbicidal activity. Moreover, it may also be used in admixture with insecticides, acaricides, nematocides, fungicides, plant growth regulators, fertilizers, soil improver and the like.

The compound (I) of the present invention can be used as an active ingredient of herbicides to be employed for paddy fields, upland fields, orchards, pusturelands, lawns, forests and non-agricultural fields.

When the compound (I) of the present invention is used as an active ingredient of herbicides, the dosage thereof is usually in the range of 0.005 to 40 grams, preferably 0.01 to 20 grams per are, although it may vary depending on the prevailing weather conditions, formulation type employed, application timing, type of application, soil involved, crop and weed species, and the like. A designated amount of the compound (I) formulated in the form of an emulsifiable concentrate, wettable powder, flowable or the like may usually be employed by diluting it with water at a volume of about 1 to 10 liters per are, if necessary, with addition of an adjuvant such as a spreading agent. The compound (I) formulated in the form of a flowable or granules may usually be applied without dilution.

Examples of the adjuvant include, in addition to the surfactants as described above, polyoxyethylene resin acids (esters), ligninsulfonates, abietates, dinaphthylmethanedisulfonates, crop oil concentrates, and crop oils such as soybean oil, corn oil, cotton seed oil and sunflower oil.

The compound (I) of the present invention can also be used as an active ingredient of harvestaid agents such as defoliants for cotton (*Gossypium hirsutum*) and desiccating agents for potato (*Solanum tuberosum*).

The present invention will be explained in more detail with reference to Preparation Examples, Formulation Examples and Test Examples, which are not to be construed to limit the scope thereof.

The following Preparation Examples will illustrate typical embodiments of the compound (I) according to the present invention.

PREPARATION EXAMPLE 1

To a solution of 1 (5 amino-4 chloro 2 -fluorophenyl)-3-methyl-4-trifluoromethyl 1,3 dihydropyrimidine-2,6 -dione (2.3 g) dissolved in chloroform (10 g), ethyl α-bromopropionate (1.6 g) was added, and this mixture was stirred and heated at 100° C. to 130° C. without any reflux condenser for 6 hours. After completion of the reaction, the reaction mixture was cooled, and the precipitate was purified by silica gel chromatography (developing solvent: chloroform) to give 1.0 g of the compound (I) wherein $R_1$ is methyl and $R^2$ is ethyl (Compound No. 10).

PREPARATION EXAMPLE 2

To a solution of 1-(5'-amino-4'-chloro-2'-fluorophenyl)-3-methyl-4 trifluoromethyl-1,3-dihydropyrimidine-2,6-dione (1.0 g) dissolved in chloroform (10 g), cyclopentyl α-bromopropionate (1.0 g) is added, and this mixture is stirred and heated at 100° C. to 130° C. without any reflux condenser for 6 hours. After completion of the reaction, the precipitate is purified by silica gel chromatography (developing solvent: chloroform) to give the compound (I) wherein $R^1$ is methyl and $R^2$ is cyclopentyl (Compound No. 33).

According to the same procedures as described above, it is possible to obtain various compounds (I) as shown in Table 1.

TABLE 1

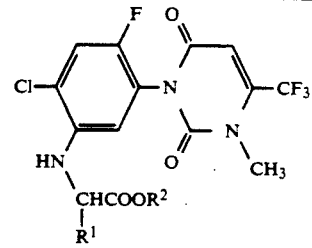

(I)

| Compound No. | $R^1$ | $R^2$ | Physical Properties |
|---|---|---|---|
| 1 | H | CH₃ | m.p. 138–139° C. |
| 2 | H | C₂H₅ | |
| 3 | H | n-C₃H₇ | |
| 4 | H | i-C₃H₇ | |
| 5 | H | n-C₄H₉ | |
| 6 | H | i-C₄H₉ | |
| 7 | H | s-C₄H₉ | |
| 8 | H | n-C₅H₁₁ | ¹H-NMR(CDCl₃, 60 MHz)δppm: 0.9 (3H, bt), 1.2–2.08(6H, m), 3.5(3H, bs), 3.85 (2H, d, J=5Hz), 4.2 (2H, t), 5.0(1H, t, J=5Hz), 6.3(1H, s), 6.4(1H, d, J=8Hz), 7.2(1H, d, J=10Hz). |
| 9 | CH₃ | CH₃ | ¹H-NMR(CDCl₃, 60 MHz)δppm: 1.5 (3H, d, J=7Hz), 3.47 (3H, bs), 3.65(3H, s), 4.0(1H, t, d, J=7Hz (t), 7Hz(d)), 4.7(1H, d, J=7Hz), 6.25(1H, s), 6.38 (1H, d, J=7 Hz), 7.13(1H, d, J=10Hz). |
| 10 | CH₃ | C₂H₅ | ¹H-NMR(CDCl₃, 60 MHz)δppm: 1.2 (3H, t, J=7Hz), 1.5 (3H, d, J=7Hz), 3.45 (3H, bs), 4.1(2H, q, J=7Hz), 3.7–4.3 (1H, m,) 4.4–5.0(1H, m), 6.2(1H, s), 6.33 (1H, d, J=7Hz), 7.1 (1H, d, J=10Hz). |
| 11 | CH₃ | n-C₃H₇ | |
| 12 | CH₃ | i-C₃H₇ | |
| 13 | CH₃ | n-C₄H₉ | ¹H-NMR(CDCl₃, 60 MHz)δppm: 0.6–1.1(3H, bt), 1.2–1.8(4H, m), 1.45(3H, d, J=6Hz), 3.46(3H, bs), 3.7–4.3 (3H, m), 4.78(1H, d, J=8Hz), 6.23(1H, s), 6.38(1H, d, J=7Hz), 7.14(1H, d, J=10Hz). |

TABLE 1-continued

| Compound No. | $R^1$ | $R^2$ | Physical Properties |
|---|---|---|---|
| 14 | CH₃ | i-C₄H₉ | |
| 15 | CH₃ | s-C₄H₉ | |
| 16 | CH₃ | n-C₅H₁₁ | |
| 17 | H | ▷ (cyclopropyl) | |
| 18 | H | (cyclobutyl) | |
| 19 | H | (cyclopentyl) | |
| 20 | H | (cyclohexyl) | |
| 21 | H | 2-methylcyclohexyl (CH₃) | |
| 22 | H | 3-methylcyclohexyl (CH₃) | |
| 23 | H | 4-methylcyclohexyl (CH₃) | |
| 24 | H | 2-ethylcyclohexyl (C₂H₅) | |
| 25 | H | 3-ethylcyclohexyl (C₂H₅) | |
| 26 | H | 4-ethylcyclohexyl (C₂H₅) | |

TABLE 1-continued

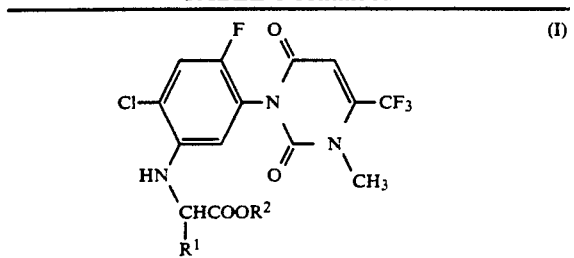

| Compound No. | R¹ | R² | Physical Properties |
|---|---|---|---|
| 27 | H | 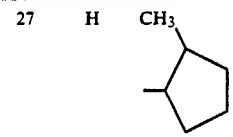 | |
| 28 | H | 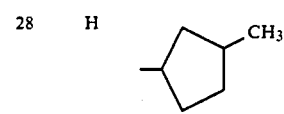 | |
| 29 | H | n-C₃H₇ 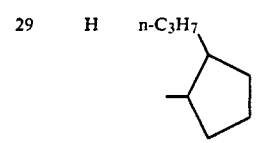 | |
| 30 | H | 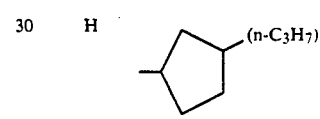 | |
| 31 | CH₃ | 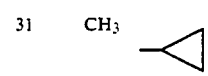 | |
| 32 | CH₃ | 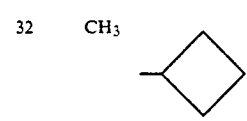 | |
| 33 | CH₃ | 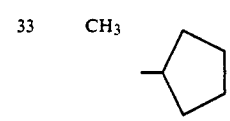 | |
| 34 | CH₃ | 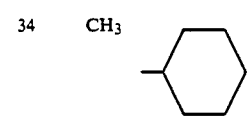 | |
| 35 | CH₃ | CH₃ 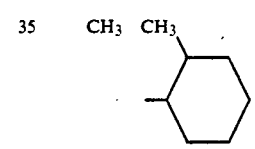 | |
| 36 | CH₃ | CH₃ 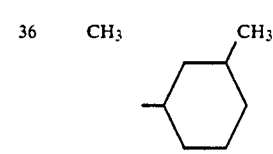 | |

TABLE 1-continued

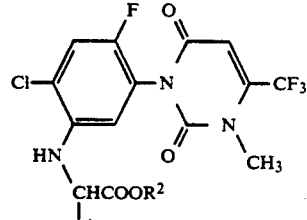

| Compound No. | R¹ | R² | Physical Properties |
|---|---|---|---|
| 37 | CH₃ | 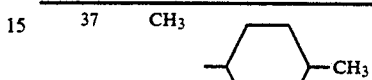 | |
| 38 | CH₃ | C₂H₅ 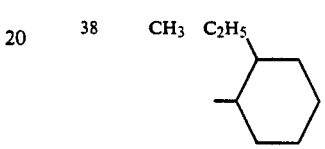 | |
| 39 | CH₃ | C₂H₅ 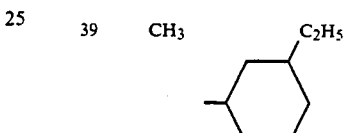 | |
| 40 | CH₃ | 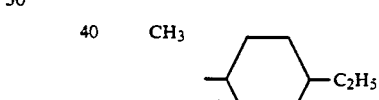 | |
| 41 | CH₃ | CH₃ 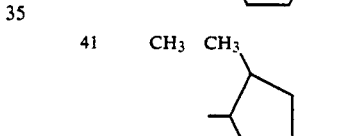 | |
| 42 | CH₃ | CH₃ 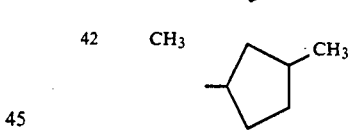 | |
| 43 | CH₃ | n-C₃H₇ 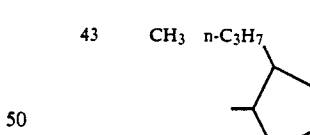 | |
| 44 | CH₃ | 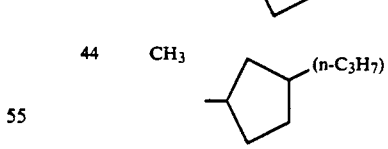 | |

The following Formulation Examples will illustrate practical embodiments of the herbicidal composition according to the present invention wherein parts are by weight. The compound number of the active ingredient corresponds to that shown in Table 1.

Formulation Example 1

Fifty parts of any one of Compound Nos. 1 and 10, 3 parts of calcium ligninsulfonate, 2 parts of sodium laurylsulfate and 45 parts of synthetic hydrated silica are well mixed while being powdered to obtain a wettable powder.

Formulation Example 2

Five parts of any one of Compound Nos. 1, 8–10 and 13, 14 parts of polyoxyethylene styrylphenyl ether, 6 parts of calcium dodecylbenzenesulfonate, 35 parts of xylene and 40 parts of cyclohexanone are well mixed to obtain an emulsifiable concentrate.

Formulation Example 3

One part of any one of Compound Nos. 1 and 10, 1 part of synthetic hydrated silica, 2 parts of calcium ligninsulfonate, 30 parts of bentonite and 66 parts of kaolin clay are well mixed while being powdered. The mixture is then kneaded with water, granulated and dried to obtain granules.

Formulation Example 4

Twenty five parts of any one of Compound Nos. 1 and 10, 3 parts of polyoxyethylene sorbitan monooleate, 3 parts of CMC and 69 parts of water are mixed, and the mixture is pulverized until the particle size becomes less than 5 microns to obtain a flowable.

The biological data of the compound (I) will be illustrated in the following Test Examples wherein the herbicidal activity and phytotoxicity are shown with an index 0, 1, 2, 3, 4 or 5, the numeral "0" indicating no or little difference in the degree of germination or growth of test plants (weeds and crop plants) at the time of the examination in comparison with the untreated plants and the numeral "5" indicating the complete inhibition or death of the test plants. The compound number in the biological data corresponds to that shown in Table 1 and the compounds used for comparison are designated by the respective compound numbers shown in Table 2.

TABLE 2

| Compound No. | Structure | Remarks |
|---|---|---|
| A | 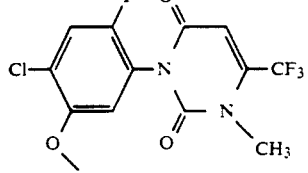 | Disclosed in the U.S. Pat. No. 4,859,229. |
| B | 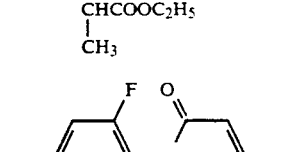 | Disclosed in the U.S. Pat. No. 5,084,084. |

TEST EXAMPLE 1

Cylindrical plastic pots (diameter, 10 cm; height, 10 cm) were filled with upland field soil, and the seeds of Japanese millet (Echinochloa frumentacea), tall morningglory (Ipomoea purpurea) and velvetleaf (Abutilon theophrasti) were sowed therein and covered with soil. A designated amount of the test compound formulated in an emulsifiable concentrate according to Formulation Example 2 was diluted with water, and the dilution was sprayed onto the soil surface by means of a small sprayer at a spray volume of 10 liters per are. The test plants were grown in a greenhouse for 20 days, and the herbicidal activity was examined. The results are shown in Table 3.

TABLE 3

| Test compound No. | Dosage (g/are) | Herbicidal activity | | |
|---|---|---|---|---|
| | | Japanese millet | Tall morning-glory | Velvet-leaf |
| 1 | 5 | 5 | 5 | 5 |
| 8 | 5 | 5 | 5 | 5 |
| 9 | 5 | 5 | 5 | 5 |
| 10 | 5 | 5 | 5 | 5 |
| 13 | 5 | 5 | 5 | 5 |

TEST EXAMPLE 2

Cylindrical plastic pots (diameter, 10 cm; height, 10 cm) were filled with upland field soil, and the seeds of tall morningglory (Ipomoea purpurea), radish (Raphanus sativus) and velvetleaf (Abutilon theophrasti) were sowed therein, followed by cultivation of these test plants in a greenhouse for 10 days. A designated amount of the test compound formulated in an emulsifiable concentrate according to Formulation Example 2 was diluted with water containing a spreading agent, and the dilution was sprayed over the foliage of the test plants by mean of a small sprayer at a spray volume of 10 liters per are. The test plants were further grown in the greenhouse for 20 days, and the herbicidal activity was examined. The results are shown in Table 4.

TABLE 4

| Test compound No. | Dosage (g/are) | Herbicidal activity | | |
|---|---|---|---|---|
| | | Tall morning-glory | Radish | Velvet-leaf |
| 1 | 0.31 | 5 | 5 | 5 |
| 8 | 0.31 | 5 | 5 | 5 |
| 9 | 0.31 | 5 | 5 | 5 |
| 10 | 0.31 | 5 | 5 | 5 |

TABLE 4-continued

| Test compound No. | Dosage (g/are) | Herbicidal activity | | |
|---|---|---|---|---|
| | | Tall morning-glory | Radish | Velvet-leaf |
| 13 | 0.31 | 5 | 5 | 5 | plants were generally at the 1 to 4 leaf stage and in 2 to 12 cm height, although growing stage of the test plants varied depending on their weed species. The test plants were further grown in the greenhouse for 18 days, and the herbicidal activity was examined. The results are shown in Table 6.

TABLE 6

| Test compound No. | Dosage (g/are) | Herbicidal activity | | | | | | | |
|---|---|---|---|---|---|---|---|---|---|
| | | Tall morning-glory | Common cocklebur | Velvet leaf | Sicklepod | Black night-shade | Barnyard-grass | Johnson grass | Giant fox-tail |
| 1 | 2.5 | 5 | 5 | 5 | 5 | 5 | 5 | 5 | 5 |
|  | 0.63 | 5 | 5 | 5 | 4 | 5 | 5 | 5 | 4 |
| 8 | 2.5 | 5 | 5 | 5 | 5 | 5 | 5 | 5 | 5 |
|  | 0.63 | 5 | 5 | 5 | 4 | 5 | 5 | 5 | 4 |
| 9 | 2.5 | 5 | 5 | 5 | 5 | 5 | 5 | 5 | 5 |
|  | 0.63 | 5 | 5 | 5 | 4 | 5 | 5 | 5 | 5 |
| 10 | 2.5 | 5 | 5 | 5 | 5 | 5 | 5 | 5 | 5 |
|  | 0.63 | 5 | 5 | 5 | 4 | 5 | 5 | 5 | 5 |
| 13 | 2.5 | 5 | 5 | 5 | 5 | 5 | 5 | 5 | 5 |
|  | 0.63 | 5 | 5 | 5 | 4 | 5 | 5 | 5 | 5 |

TEST EXAMPLE 3

Cylindrical plastic pots (diameter, 8 cm; height, 12 cm) were filled with paddy field soil, and the seeds of barnyardgrass (*Echinochloa oryzicola*) and broad-leaf weeds (e.g., common falsepimpernel (*Lindernia procumbens*), Indian toothcup (*Rotala indica*) and waterwort (*Elatine triandra*)) were mixed with the soil in 1 to 2 cm depth. Water was poured therein to make a flooded condition, and rice seedlings at the 2 leaf stage were transplanted therein and the test plants were grown in a greenhouse. After 6 days (i.e., at that time the weeds began to germinate), a designated amount of the test compound formulated in an emulsifiable concentrate according to Formulation Example 2 was diluted with water (5 ml), and the dilution was applied to the water surface. The test plants were grown in the greenhouse for 20 days, and the herbicidal activity and phytotoxicity were examined. The results are shown in Table 5.

TABLE 5

| Test compound No. | Dosage (g/are) | Phyto-toxicity Rice | Herbicidal activity | |
|---|---|---|---|---|
| | | | Barnyard grass | Broad-leaf weeds |
| 1 | 0.16 | 1 | 4 | 5 |
| 10 | 0.16 | 1 | 5 | 5 |

TEST EXAMPLE 4

Vats (area, 33×23 cm²; height, 11 cm) were filled with upland field soil, and the seeds of tall morning-glory (*Ipomoea purpurea*), common cocklebur (*Xanthium pensylvanicum*), velvetleaf (*Abutilon theophrasti*), sicklepod (*Cassia obtusifolia*), black nightshade (*Solanum nigrum*), barnyardgrass (*Echinochloa crus-galli*), Johnsongrass (*Sorghum halepense*) and giant foxtail (*Setaria faberi*) were sowed therein, followed by cultivation of these test plants in a greenhouse for 16 days. A designated amount of the test compound formulated in an emulsifiable concentrate according to Formulation Example 2 was diluted with water, and the dilution was uniformly sprayed all over the foliage of the test plants by means of a small sprayer at a spray volume of 10 liters per are. At the time of the application, the test plants were generally at the 1 to 4 leaf stage and in 2 to 12 cm height, although growing stage of the test plants varied depending on their weed species. The test plants were further grown in the greenhouse for 18 days, and the herbicidal activity was examined. The results are shown in Table 6.

TEST EXAMPLE 5

Vats (area, 33×23 cm²; height, 11 cm) were filled with upland field soil, and the seeds of corn (*Zea mays*), common cocklebur (*Xanthium pensylvanicum*), barnyardgrass (*Echinochloa crus-galli*), Johnsongrass (*Sorghum halepense*) and giant foxtail (*Setaria faberi*) were sowed therein, followed by cultivation of the test plants in a greenhouse for 16 days. A designated amount of the test compound formulated in an emulsifiable concentrate according to Formulation Example 2 was diluted with water, and the dilution was uniformly sprayed all over the foliage of the test plants by means of a small sprayer at a spray volume of 10 liters per are. At the time of the application, the test plants were generally at the 1 to 4 leaf stage and in 2 to 12 cm height, although growing stage of the test plants varied depending on their weed species. The test plants were further grown in the greenhouse for 18 days, the herbicidal activity and phytotoxicity were examined. The results are shown in Table 7.

TABLE 7

| Test com-pound No. | Dosage (g/are) | Phytoto-xicity Corn | Herbicidal activity | | | |
|---|---|---|---|---|---|---|
| | | | Common cockle-bur | Barn-yard-grass | John-son-grass | Giant fox-tail |
| 10 | 0.16 | 1 | 5 | 5 | 4 | 5 |
| A | 0.16 | 1 | 5 | 5 | 2 | 2 |
| B | 0.16 | 1 | 5 | 5 | 3 | 2 |

TEST EXAMPLE 6

Vats (area, 33×23 cm²; height, 11 cm) were filled with upland field soil, and the seeds of wheat (*Triticum aestivum*), pale smartweed (*Polygonum lapathifolium*), persian speedwell (*Veronica persica*) and field pansy (*Viola arvensis*) were sowed therein, followed by cultivation of these test plants in a greenhouse for 31 days. A designated amount of the test compound formulated in an emulsifiable concentrate according to Formulation Example 2 was diluted with water, and the dilution was uniformly sprayed all over the foliage of the test plants by mean of a small sprayer at a spray volume of 10 liters per are. At the time of the application, the test plants were generally in the 1 to 4 leaf stage and in 2 to 12 cm height, although growing stage of the test plants varied depending on the weed species. The test plants were further grown in the greenhouse for 25 days, and the herbicidal activity and phytotoxicity were examined. The results are shown in Table 8.

TABLE 8

| Test compound No. | Dosage (g/are) | Phytotoxicity Wheat | Herbicidal activity | | |
|---|---|---|---|---|---|
| | | | Pale smartweed | Persian speedwell | Field pansy |
| 1 | 0.63 | 1 | 5 | 5 | 5 |
| | 0.16 | 1 | 4 | 5 | 4 |

TEST EXAMPLE 7

Vats (area, 33×23 cm²; height, 11 cm) were filled with upland field soil, and the seeds of common chickweed (*Stellaria media*), downy brome (*Bromus tectorum*), wild oats (*Avena fatua*), blackgrass (*Alopecurus myosuroides*) and annual bluegrass (*Poa annua*) were sowed therein and covered with soil in 1 to 2 cm depth. A designated amount of the test compound formulated in an emulsifiable concentrate according to Formulation Example 2 was diluted with water, and the dilution was sprayed onto the soil surface by mean of a small sprayer at a spray volume of 10 liters per are. The test plants were grown in a greenhouse for 25 days, and the herbicidal activity was examined. The results are shown in Table 9.

TABLE 9

| Test compound No. | Dosage (g/are) | Herbicidal activity | | | | |
|---|---|---|---|---|---|---|
| | | Common chickweed | Downy brome | Wild oats | Blackgrass | Annual bluegrass |
| 9 | 2.5 | 5 | 5 | 5 | 4 | 4 |
| 10 | 2.5 | 5 | 5 | 5 | 4 | 4 |
| 13 | 2.5 | 5 | 5 | 5 | 4 | 3 |
| A | 2.5 | 1 | 1 | 5 | 4 | 2 |
| B | 2.5 | 5 | 2 | 3 | 1 | 1 |

What is claimed is:

1. A compound of the general formula:

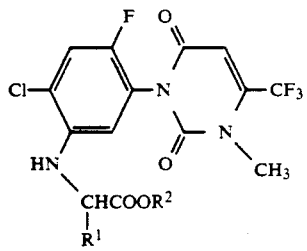

wherein $R^1$ is hydrogen or methyl, and $R^2$ is $C_1$-$C_7$ alkyl or $C_3$-$C_7$ cycloalkyl optionally substituted with $C_1$-$C_3$ alkyl.

2. A compound according to claim 1, wherein $R^1$ is methyl.

3. A compound according to claim 2, wherein $R^2$ is $C_1$-$C_5$ alkyl.

4. A compound according to claim 3, wherein $R^2$ is methyl.

5. A compound according to claim 3, wherein $R^2$ is ethyl.

6. A compound according to claim 3, wherein $R^2$ is n-butyl.

7. A compound according to claim 3, wherein $R^2$ is cyclopentyl.

8. A compound according to claim 1, wherein $R^1$ is hydrogen and $R^2$ is n-pentyl.

9. A herbicidal composition comprising as an active ingredient a herbicidally effective amount of the compound according to claim 1, and an inert carrier or diluent.

10. A method for exterminating undesired weeds, which comprises applying the herbicidal composition according to claim 9 to the area where undesired weeds grow or will grow.

11. A compound according to claim 1, wherein $R^1$ is hydrogen and $R^2$ is methyl.

12. A compound according to claim 1, wherein $R^2$ is selected from the group consisting of cycloproply, cyclobutyl and cyclopentyl.

13. A compound according to claim 1, wherein $R^2$ is selected from the group consisting of

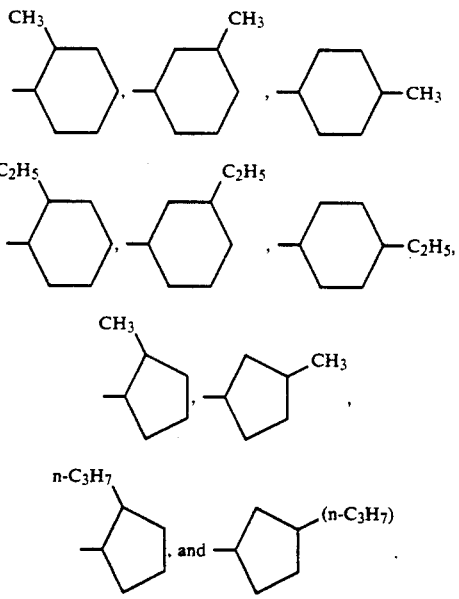

* * * * *